US010470802B2

(12) United States Patent
Sournac et al.

(10) Patent No.: US 10,470,802 B2
(45) Date of Patent: Nov. 12, 2019

(54) REVISION ASSEMBLY FOR AN ITEM OF VERTEBRAL OSTEOSYNTHESIS EQUIPMENT

(71) Applicant: MEDICREA INTERNATIONAL, Neyron (FR)

(72) Inventors: Denys Sournac, Reyrieux (FR); Thomas Mosnier, Anthon (FR); David Ryan, Collonges au Mont d'Or (FR)

(73) Assignee: MEDICREA International, Neyron (FR)

( * ) Notice: Subject to any disclaimer, the term of this patent is extended or adjusted under 35 U.S.C. 154(b) by 581 days.

(21) Appl. No.: 14/783,882

(22) PCT Filed: Apr. 10, 2014

(86) PCT No.: PCT/IB2014/060614
§ 371 (c)(1),
(2) Date: Oct. 12, 2015

(87) PCT Pub. No.: WO2014/170803
PCT Pub. Date: Oct. 23, 2014

(65) Prior Publication Data
US 2016/0058476 A1    Mar. 3, 2016

(30) Foreign Application Priority Data

Apr. 19, 2013 (FR) ...................................... 13 53592

(51) Int. Cl.
*A61B 17/70* (2006.01)
*A61B 90/00* (2016.01)

(52) U.S. Cl.
CPC ...... *A61B 17/7032* (2013.01); *A61B 17/7037* (2013.01); *A61B 17/7041* (2013.01); *A61B 17/7049* (2013.01); *A61B 2090/037* (2016.02)

(58) Field of Classification Search
CPC ............ A61B 17/7041; A61B 17/7035; A61B 17/7037; A61B 17/7091
See application file for complete search history.

(56) References Cited

U.S. PATENT DOCUMENTS 5,234,431 A * 8/1993 Keller ................ A61B 17/7007
606/287
5,628,740 A * 5/1997 Mullane ............. A61B 17/7037
606/307

(Continued)

FOREIGN PATENT DOCUMENTS

WO       WO98/55038        12/1998

*Primary Examiner* — Jacqueline T Johanas
(74) *Attorney, Agent, or Firm* — Defillo & Associates, Inc; Evelyn A Defillo

(57) ABSTRACT

This item of vertebral osteosynthesis equipment includes at least one bone anchoring member (51) including a proximal threaded pin, at least one connecting part (52) with a hole (58) for the engagement of same on the proximal threaded pin, and at least one nut intended to be screwed onto the thread provided on the outside of the pin (54) in order to receive the nut. According to the invention, the revision assembly (1) includes a threaded extension rod (2) having a widened end (6) that defines a threaded axial cavity (10), the threaded axial cavity (10) being dimensioned to allow the threaded extension rod (2) to be screwed onto the thread provided on the threaded pin (54); the hole (58) provided in the connecting part (52) has a diameter such that it can receive said widened end (6) of the threaded extension rod (2) therethrough; and the revision assembly (1) includes a so-called "reassembly" nut suitable for being screwed onto the threaded extension rod (2).

8 Claims, 4 Drawing Sheets

(56) References Cited

U.S. PATENT DOCUMENTS

| | | | | |
|---|---|---|---|---|
| 6,267,765 B1* | 7/2001 | Taylor | A61B 17/7007 | 606/86 A |
| 7,572,280 B2* | 8/2009 | Dickinson | A61B 17/7007 | 606/266 |
| 7,591,836 B2* | 9/2009 | Dick | A61B 17/7035 | 606/246 |
| 8,308,775 B2 | 11/2012 | Clement | | |
| 8,372,122 B2* | 2/2013 | Winslow | A61B 17/7005 | 606/264 |
| 8,672,979 B2* | 3/2014 | Bishop | A61B 17/7037 | 606/246 |
| 8,915,944 B2* | 12/2014 | Pisharodi | A61B 17/7001 | 606/246 |
| 9,186,184 B2* | 11/2015 | Janowski | A61B 17/7038 | |
| 2003/0028191 A1* | 2/2003 | Shluzas | A61B 17/7035 | 606/278 |
| 2004/0092930 A1* | 5/2004 | Petit | A61B 17/7037 | 606/264 |
| 2005/0234454 A1* | 10/2005 | Chin | A61B 17/7007 | 606/287 |
| 2005/0277923 A1* | 12/2005 | Sweeney | A61B 17/1671 | 623/17.11 |
| 2006/0025769 A1* | 2/2006 | Dick | A61B 17/7035 | 606/86 A |
| 2006/0167455 A1* | 7/2006 | Clement | A61B 17/7037 | 606/264 |
| 2007/0149973 A1* | 6/2007 | Clement | A61B 17/7037 | 606/301 |
| 2007/0173817 A1* | 7/2007 | Sournac | A61B 17/7037 | 606/250 |
| 2008/0195150 A1* | 8/2008 | Bishop | A61B 17/7037 | 606/246 |
| 2010/0331897 A1* | 12/2010 | Lindner | A61B 17/7041 | 606/305 |
| 2011/0196424 A1* | 8/2011 | Bishop | A61B 17/7037 | 606/264 |
| 2012/0277799 A1* | 11/2012 | Winslow | A61B 17/7005 | 606/264 |

* cited by examiner

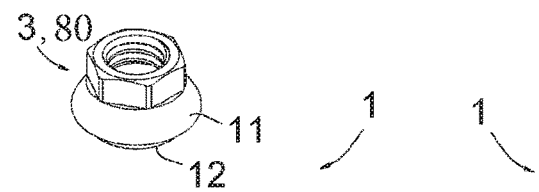
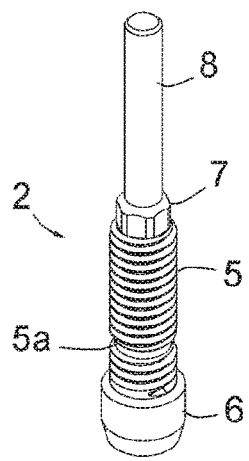
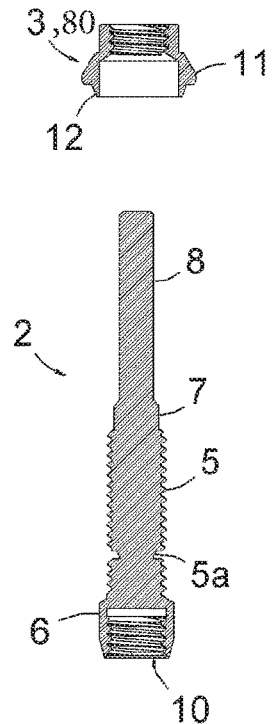
FIG. 1
FIG. 2
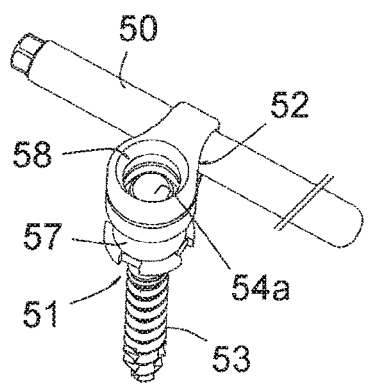
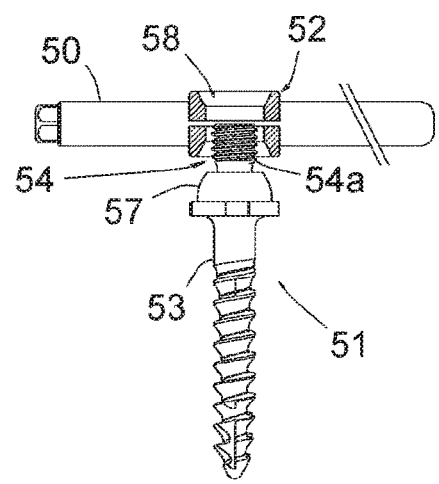
FIG. 3
FIG. 4

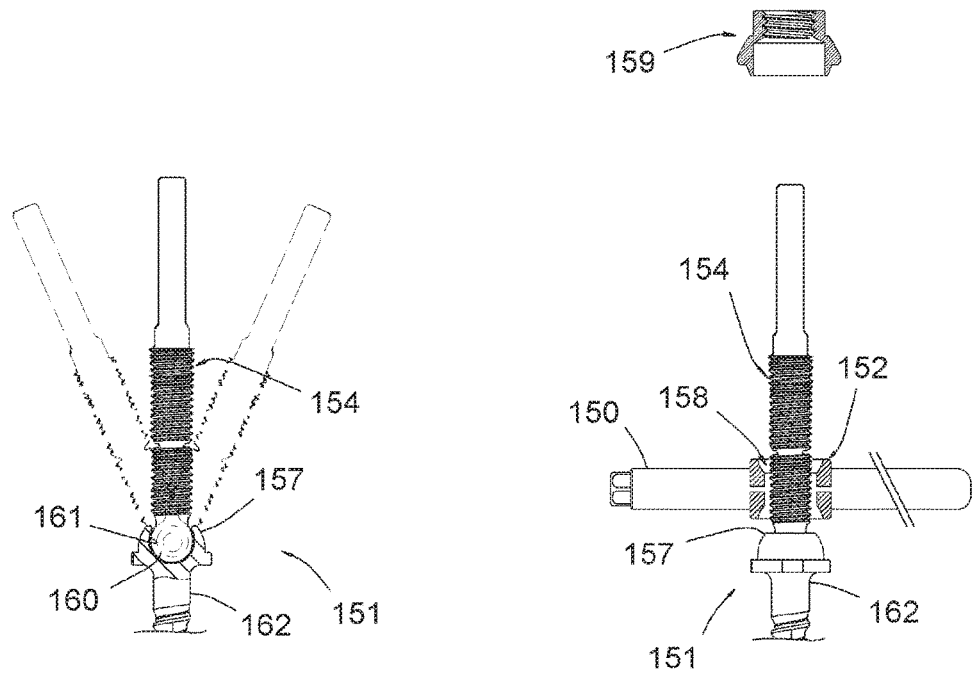
FIG. 12
Prior art
FIG. 13
Prior art
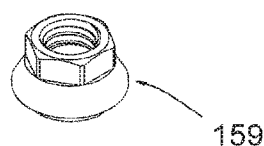
FIG. 14
Prior art

REVISION ASSEMBLY FOR AN ITEM OF VERTEBRAL OSTEOSYNTHESIS EQUIPMENT

CROSS REFERENCE TO RELATED APPLICATION

This application is a national stage entry of PCT/IB2014/060614 filed Apr. 10, 2014, under the International Convention claiming priority over French Patent Application No. 1353592 filed Apr. 19, 2013.

FIELD OF THE INVENTION

The present invention relates to a revision assembly for an item of vertebral osteosynthesis equipment.

A vertebral osteosynthesis equipment comprises, in a manner well known in itself:

at least one rigid bar designed to connect several vertebrae, bone anchoring members, such as screws or laminar hooks, connecting parts making it possible to connect the bar(s) to the bone anchoring members, and tightening means making it possible to exert a pulling force on the bone anchoring members so as to correct the position of the vertebrae relative to the reference formed by the bar. The equipment, once in place, makes it possible to immobilize the vertebrae in their correction position.

BACKGROUND OF THE INVENTION

Known items of equipment of this type are in particular described by patent application or patent publications no. WO 98/55038 and U.S. Pat. No. 8,308,775, or by French patent application publication no. FR 2,856,581 A1. In these items of equipment, each bone anchoring member is in the form of a "polyaxial" pedicle screw, i.e., comprising an articulated proximal threaded pin; the corresponding connecting part is designed to be engaged on that proximal threaded pin using a hole that it comprises; said tightening means is made up of a nut designed to be screwed on the threaded proximal pin and to bear against the connecting part. Tightening the nut makes it possible to pull the screw toward the connecting part until a bearing surface arranged on the screw comes into contact with the connecting part. This gradual pulling makes it possible to correct the position of the vertebrae. Once said bearing surface is placed against the connecting part, the nut is pulled tight and the part of the pin protruding past the nut is broken. To favor this breaking, the pin comprises a thinner portion with a lower resistance; after breaking, the threaded proximal pin is reduced to a remaining portion of that pin.

With such items of equipment including pedicle screws, positioning the screws perfectly in the pedicles of the vertebrae is problematic. Indeed, if a screw deviates from its correct position, it may cause compression or even damage of a nerve ending, creating significant pain for the patient. In such a case, it is necessary to operate on the patient again in order to correct the position of the screw. This correction may, however, lead to a noticeable change in the position of the screw with respect to the corresponding connecting part, making it difficult or even impossible to resituate the nut on the remaining portion of the threaded pin.

The same problem of resituating the nut exists when the screw comprises a short, unbreakable proximal pin, i.e., an item of equipment whose reduction capacity is essentially based on the ancillary associated with that item of equipment.

The aforementioned documents, and in particular document FR 2,856,581 A1, do not address this specific problem and therefore do not provide a solution thereto. In the absence of such a solution, either one may decide not to correct the incorrect position of the bone anchoring member, or it is necessary to replace the entire item of equipment, which involves a long and complex procedure.

SUMMARY OF THE INVENTION

The present invention aims to resolve this specific problem.

The revision assembly to which it relates can be used with an item of vertebral osteosynthesis equipment comprising at least one bone anchoring member including a threaded proximal pin, at least one connecting part comprising a hole for its engagement on that threaded proximal pin, and at least one nut designed to be screwed on the thread outwardly comprised by the pin for receiving that nut.

According to the invention, the revision assembly comprises a threaded extension rod having a widened end that defines a threaded axial cavity, said threaded axial cavity being dimensioned to allow the threaded extension rod to be screwed onto said thread provided on the threaded pin;

the hole provided in said connecting part has a diameter such that it is capable to receive said widened end of the threaded extension rod therethrough; and the revision assembly comprises a so-called "reassembly" nut suitable for being screwed onto said threaded extension rod.

Thus, the threaded extension rod is able to be engaged through the hole comprised by the connecting part, then to be screwed on the remaining portion of the threaded pin, and said reassembly nut is placed on the threaded extension rod. The revision assembly according to the invention therefore makes it possible to once again tighten the connecting part against the bone anchoring member, using that reassembly nut.

The hole comprised by said connecting part, or comprised by each connecting part when the item of equipment comprises several connecting parts, has a diameter larger than that of a traditional connecting part, given that it is designed to receive not only the threaded pin through it, but also said widened end of the threaded extension rod.

The reassembly nut can be the original nut itself if the threaded extension rod has the same diameter and has a thread identical to that of the threaded proximal pin; otherwise, that nut is a replacement nut.

The revision assembly is used as follows:

loosening the original nut of the anchoring member to be repositioned and disengaging the connecting part associated with that member;

repositioning the anchoring member;

resituating the connecting part on the threaded pin;

screwing the threaded extension rod on that threaded pin, by engaging said widened end through the hole comprised by the connecting part;

placing the reassembly nut, and sectioning the threaded extension rod passed that nut.

The anchoring member can be a pedicle screw or a laminar hook; such a pedicle screw can be "mono-axial", i.e., in which the threaded proximal pin is integral with the rest of screw, or "polyaxial", i.e., in which the threaded proximal pin is articulated relative to the rest of the screw; in such a case, the threaded proximal pin comprises means for immobilizing its rotation during placement of the threaded extension rod. These means can be formed by an articulating head with a polygonal section placed in a cavity with a corresponding shape, for example like that described by patent application publication no. FR 2,831,048; these means can also be formed by a collar secured to the pin, comprising one or more flat portions, and by a corresponding shape of the hole of the connecting part, as described in international patent application publication no. WO 98/55038.

Preferably, the threaded extension rod comprises a portion with a reduced section favoring its breakage beyond the proximal face of the reassembly nut, after the latter is completely tightened.

The proximal portion of the threaded extension rod is thus able to be broken easily past that proximal face once the placement is done.

When, as is frequently the case, the hole of the connecting part forms a proximal cup designed to receive a conical distal portion of the original nut, as described in the aforementioned international patent application publication no. WO 98/55038, the original nut may not be reused because said widened end of the threaded extension rod occupies a substantial portion of the space defined by said cup once placed on the threaded proximal pin. Said replacement nut then comprises a widened distal base allowing bearing against the proximal face of the connecting part.

This replacement nut can, however, comprise a tubular, outwardly conical distal portion, protruding from said widened distal base and dimensioned to be placed in the space existing between the connecting part and said widened end of the threaded extension rod.

This tubular distal portion thus makes it possible to occupy said remaining space and ensure perfect revision of the play between the connecting part and said threaded extension rod.

BRIEF DESCRIPTION OF THE DRAWINGS

The invention will be better understood, and other features and advantages thereof will appear, in reference to the appended diagrammatic drawing, showing, as a non-limiting example, one preferred embodiment of the relevant revision assembly.

FIG. 1 is a perspective view of the threaded extension rod and a replacement nut making up that revision assembly;

FIG. 2 is a view of that rod and that replacement nut in cross-section passing through the axis of said rod and said nut;

FIGS. 3 and 4 are perspective and partial cross-sectional views, respectively, of different parts included in an item of vertebral osteosynthesis equipment, during a first step of a method for revising the position of a "polyaxial" pedicle anchoring screw comprised by that equipment; said partial cross-section passes through the axis of the hole comprised by a connecting part that is part of that equipment;

DETAILED DESCRIPTION OF THE INVENTION

Figure 5:
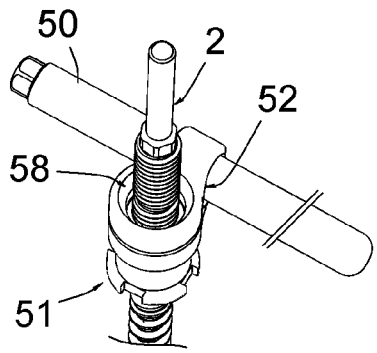
FIGS. 5, 7 and 9 are views of the item of equipment similar to FIG. 3, during successive subsequent steps of the revision method.

FIGS. 1 and 2 show a threaded extension rod 2 and a so-called "replacement" nut 3 jointly forming an assembly 1 making it possible to revise the position of a pedicle anchoring screw comprised by an item of vertebral osteosynthesis equipment.

This item of vertebral osteosynthesis equipment is of one of the well-known types in particular described by patent application or patent publications no. WO 98/55038 and U.S. Pat. No. 8,308,775. As visible in FIGS. 3 and 4, this item of equipment comprises at least one rigid bar 50 designed to connect several vertebrate to one another, several so-called "polyaxial" pedicle screws 51, i.e., including articulated threaded proximal pins 54, several connecting parts 52 comprising holes 58 for their engagement on the pins 54, and so-called "original" nuts 80, designed to be screwed on those threaded proximal pins 54 to pull the screws 51 gradually toward the connecting parts 52 until the bearing surfaces 57 comprised by the screws 51 arrive against the connecting parts 52, thus correcting the position of the vertebrae. Once said bearing surfaces 57 are placed against the connecting parts 52, said original nuts 80 are pulled tight and the parts of the pins 54 protruding past those nuts are broken. To favor this breaking, each pin comprises a portion with a reduced section, of lower resistance, such that after placement of the item of equipment, the threaded proximal pin 54 is reduced to a remaining portion 54a of that pin.

FIGS. 3 and 4 show only part of an item of vertebral osteosynthesis equipment of this type, i.e., one of the rigid bars 50, one of the pedicle screws 51 and a connecting part 52.

The pedicle screw 51 comprises a screwing base 53 to be screwed in the pedicle of a vertebra and the articulated threaded proximal pin 54; in FIGS. 3 and 4, the remaining portion 54a of this articulated threaded proximal pin 54 is illustrated.

The base 53 forms a proximal cavity for receiving a distal articulation head formed by the pin 54. The articulation head is of the type described by patent application publication no. FR 2,831,048, with a polygonal section placed in a cavity having a corresponding shape. To form the screw 51, the articulation head is engaged in the cavity, then the wall 57 of the base 53 defining the periphery of the cavity is crimped around that articulation head, according to a substantially hemispherical outer shape, as shown in FIG. 4. After crimping, the assembly is such that the articulation head is retained in said cavity and the pin 54 has a multidirectional travel relative to the base 53 while being wedged in rotation along its axis relative to that base.

The pin 54 has a cylindrical shape and is threaded at its peripheral face. It forms the aforementioned portion with a reduced section, the breaking of which creates said remaining portion 54a.

The wall 57 forms a bearing surface for the base 53 against the connecting part 52 when the aforementioned nut is completely tightened.

The connecting part 52 forms a hole 58 allowing it to be engaged on the pin 54. This hole 58 nevertheless has a wider diameter than that which is necessary for the passage of the pin 54: it also allows the passage of a widened end 6 comprised by the extension rod 6, as described below.

In reference again to FIGS. 1 and 2, it appears that the rod 2 comprises a threaded portion 5, a widened end 6 situated at one end of that threaded portion 5, a faceted portion 7 at the other end of the portion 5 and a smooth portion 8 with a smaller section, connected to the portion 7 on the side opposite the portion 5.

The threaded portion 5 has a same diameter and forms a thread identical to that of the pin 54. It is able to receive said replacement nut 3 screwed on it as described below. It comprises a portion 5a with a reduced section making it possible to break the rod 2 easily past the proximal face of the replacement nut 3 once that nut is placed and tightened.

Figure 6:
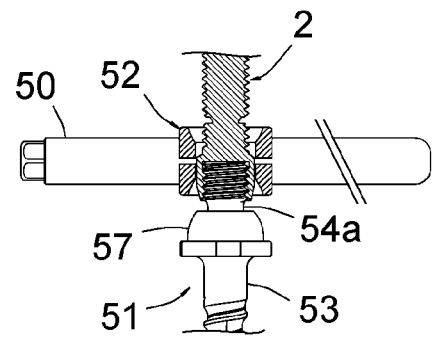
FIGS. 6, 8 and 10 are views of that equipment similar to FIG. 4, during those same steps.

The widened end 6 has a circular outer shape and an outer diameter slightly smaller than the inner diameter of the hole 58. It therefore has a cross-section such that it is capable to be engaged through that hole 58, as shown by FIGS. 5 and 6. The end 6, owing to its widened shape, delimits a tapped axial cavity 10, with an inner diameter corresponding, in addition to the functional play, to that of the remaining portion of the pin 54, and the thread of which is compatible with the thread comprised on the remaining portion 54a. The rod 2 is thus able to be screwed on the remaining portion 54a of the pin 54.

The faceted portion 7 allows the rod 2 to be rotated so that it is capable to be screwed on that remaining portion 54a.

The smooth portion 8 with a smaller section forms a rod facilitating the lowering of the nut 3 on the threaded portion 5.

The nut 3 comprises a widened distal base 11 forming a distal collar defining a wide bearing surface for bearing against the proximal face of the connecting part 52, and comprises a distal tubular portion 12, outwardly conical, protruding from the widened distal base 11. As shown in FIGS. 7 to 10, this distal tubular portion 12 is dimensioned to be placed in the space remaining between the connecting part 52, which forms a proximal conical cup at the hole 58, and the widened end 6.

In practice, the positioning of the screw 51 is revised as follows.

The patient undergoes a new operation so as to access the original nut included by the screw 51, and that nut is loosened, then removed. The connecting part 52 is separated from the screw 51, then the latter is removed and re-situated appropriately.

As shown by FIGS. 3 and 4, this change in position of the screw 51 relative to the connecting part 52, as well as the release of the tension exerted on the vertebra by the screw 51, causes the remaining portion 54a of the pin 54 not to protrude sufficiently from the part 52 to resituate the original nut.

Figure 7:
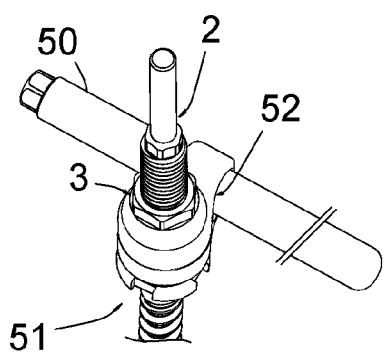
Figure 8:
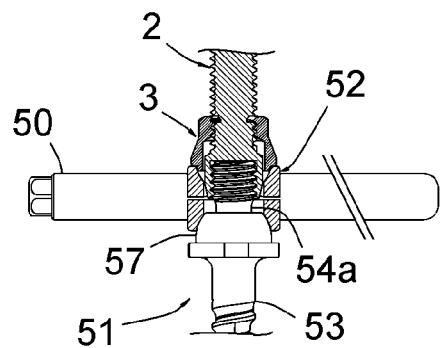

The threaded extension rod 2 is then placed by screwing on that remaining portion 54a (cf. FIGS. 5 and 6), by engaging the widened end 6 through the hole 58, then the replacement nut 3 is placed and tightened until the surface 57 is brought into contact with the connecting part 52 (cf. FIGS. 7 and 8).

Figure 9:
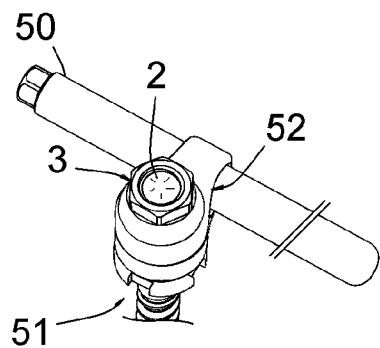
Figure 10:
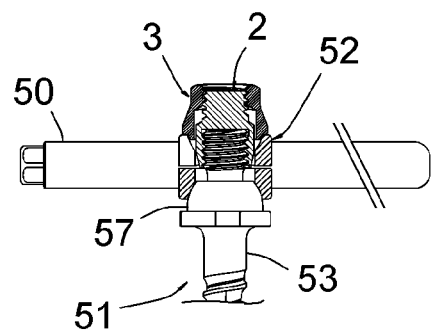

The threaded extension rod 2 is then broken at the portion 5a, which is situated near the proximal face of the nut 3 (cf. FIGS. 9 and 10).

Figure 11:
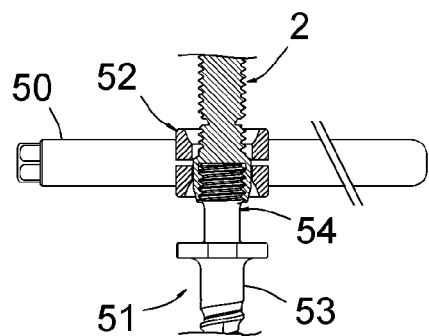
FIG. 11 is a view of the item of equipment similar to FIG. 6 in the case of a "monoaxial" pedicle anchoring screw.

FIG. 11 shows an item of equipment very similar to that described above, except that the screw 51 is "monoaxial", i.e., with a threaded proximal pin 54 being integral with the base 53.

As appears from the preceding, the invention provides an assembly having the decisive advantage of making it possible to revise the position of a pedicle screw quickly and easily.

The invention has been described above in reference to one embodiment provided as an example. Of course, it is not limited to this embodiment, but extends to all other embodiments covered by the appended claims. In particular, a breakable proximal pin 54 is described above, but of course the invention is applicable in the same way to a screw comprising a non-breakable short proximal pin, i.e., an item of equipment whose reduction capacity rests essentially on the ancillary associated with that equipment; the pedicle screw can be replaced by a laminar hook comprising a threaded proximal pin.

The invention claimed is:

1. A revision assembly comprising:
   an item of vertebral osteosynthesis equipment, the item of vertebral osteosynthesis equipment comprising at least one bone anchoring member including a threaded proximal pin having an external thread and a first diameter, at least one connecting part comprising a hole having a second diameter for the engagement of the at least one connecting part on said threaded proximal pin, the second diameter of the hole being bigger than the first diameter of the threaded proximal pin, and at least one nut to screw on the external thread of the threaded proximal pin so as to tighten the at least one connecting part between the at least one nut and a bearing surface on the at least one bone anchoring member;
   wherein:
   the revision assembly further comprises:
   a threaded extension rod having an external thread and a widened end with an outer third diameter bigger than the first diameter of the threaded proximal pin and smaller than the second diameter of the hole, said widened end defining a threaded axial cavity, said threaded axial cavity being dimensioned to allow the threaded extension rod to be screwed onto said thread provided on the threaded proximal pin;
   said second diameter of the hole provided in said connecting part being such that the hole receives said widened end of the threaded extension rod there through; and
   said at least one nut is further capable of being screwed onto said external thread of the threaded extension rod.

2. The revision assembly according to claim 1, wherein the external thread and a diameter of the threaded extension rod are identical to the external thread and first diameter of the threaded proximal pin, and the at least one nut is an original nut included in the item of vertebral osteosynthesis equipment.

3. The revision assembly according to claim 1, wherein said at least one nut comprises a replacement nut and an original nut.

4. The revision assembly according to claim 3, wherein the at least one connecting part has a proximal face and said at least one nut comprises a widened distal base allowing bearing against the proximal face of the at least one connecting part.

5. The revision assembly according to claim 4, wherein said at least one nut comprises a tubular, outwardly conical distal portion, protruding from said widened distal base and dimensioned to be placed in the space existing between the at least one connecting part and said widened end of the threaded extension rod.

6. The revision assembly according to claim 1, wherein said at least one anchoring member is a "mono-axial" pedicle screw in which the threaded proximal pin is integral with the rest of the pedicle screw.

7. The revision assembly according to claim 1, wherein the threaded extension rod comprises a portion with a reduced section favoring its breakage beyond a proximal face of the at least one nut, after the at least one nut is completely tightened.

8. A surgical method using the vertebral osteosynthesis equipment and the revision assembly according to claim 1, the method includes the following steps:
   providing the revision assembly of claim 1,
   loosening the at least one nut attached to the at least one anchoring member to be repositioned and disengaging the connecting part associated with said at least one anchoring member;
   repositioning the at least one anchoring member;
   resituating the connecting part on the threaded proximal pin;
   screwing the threaded extension rod on the threaded proximal pin by engaging said widened end through the hole of the connecting part;
   placing the at least one nut on the threaded extension rod; and
   breaking the threaded extension rod past the at least one nut.

* * * * *